United States Patent

Barton et al.

[11] Patent Number: 4,689,410
[45] Date of Patent: Aug. 25, 1987

[54] NOVEL 23-DIHYDRO-OXAZOLYL STEROIDS

[75] Inventors: Derek H. R. Barton; Samir Z. Zard; Jocelyne Wozniak, all of Gif-sur-Yvette, France

[73] Assignee: Roussel Uclaf, Paris, France

[21] Appl. No.: 787,657

[22] Filed: Oct. 16, 1985

[30] Foreign Application Priority Data

Oct. 16, 1984 [FR] France ................. 84 15815

[51] Int. Cl.$^4$ ............................................. C07J 17/00
[52] U.S. Cl. ................................................ 540/108
[58] Field of Search ................ 260/239.55 R; 540/108

[56] References Cited

U.S. PATENT DOCUMENTS

| 4,401,596 | 8/1983 | Barton et al. | 260/239.55 R |
| 4,434,080 | 2/1984 | Barton et al. | 260/397.4 |
| 4,460,509 | 7/1984 | Mosbach et al. | 260/239.55 R |

Primary Examiner—Leonard Schenkman
Attorney, Agent, or Firm—Bierman & Muserlian

[57] ABSTRACT

Novel 23-dihydro-oxazolyl steroids of the formula

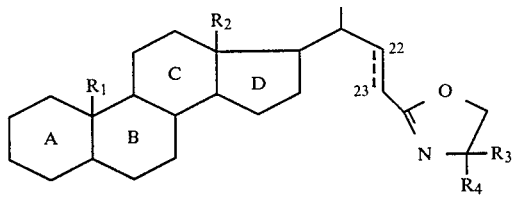

wherein $R_1$ is selected from the group consisting of hydrogen and methyl, $R_2$ is selected from the group consisting of methyl and ethyl, $R_3$ and $R_4$ are individually selected from the group consisting of hydrogen and alkyl of 1 to 4 carbon atoms, the A, B, C and D rings may contain 1 to 3 double bonds and may be optionally substituted with one or more members of the group consisting of —OH, protected hydroxyl, =O, protected keto, halogen alkyl or alkoxy of 1 to 4 carbon atoms and alkenyl and alkynyl of 2 to 4 carbon atoms and the dotted line indicates the optional presence of a second bond useful for the preparation of 20-keto-pregnanes and novel intermediates.

9 Claims, No Drawings

NOVEL 23-DIHYDRO-OXAZOLYL STEROIDS

STATE OF THE ART

U.S. Pat. Nos. 4,401,596 and 4,434,080 describe related compounds.

OBJECTS OF THE INVENTION

It is an object of the invention to provide the novel compounds of formula I and a novel process and novel intermediates for their preparation.

It is another object of the invention to provide a novel process for the preparation of 20-keto-pregnanes from the compounds of formula I.

These and other objects and advantages of the invention will become obvious from the following detailed description.

THE INVENTION

The novel 23-dihydro-oxazolyl-steroids of the invention have the formula

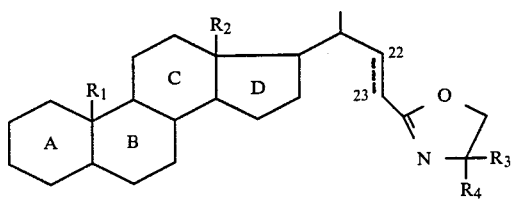

wherein $R_1$ is selected from the group consisting of hydrogen and methyl, $R_2$ is selected from the group consisting of methyl and ethyl, $R_3$ and $R_4$ are individually selected from the group consisting of hydrogen and alkyl of 1 to 4 carbon atoms, the A, B, C and D rings may contain 1 to 3 double bonds and may be optionally substituted with one or more members of the group consisting of —OH, protected hydroxyl, =O, protected keto, halogen, alkyl or alkoxy of 1 to 4 carbon atoms and alkenyl and alkynyl of 2 to 4 carbon atoms and the dotted line indicates the optional presence of a second bond.

When the A,B,C, and D rings contain one or more double bonds, they are preferred to be double bonds at 1(2), 4(5), 5(6) or 9(11), or a system of conjugated double bonds at 3(4) and 5(6) or at 4(5) and 6(7) or an aromatic system of three double bonds 1,3,5 or a system of three double bonds 1(2), 4(5), 6(7). Nevertheless, it is preferred to use products without double bonds.

When the A,B,C, and D rings are substituted by one or more hydroxyl functions, they are preferred to be one or more hydroxyl groups at positions 3,6,7,11 and/or 12. When the A,B,C and D rings are substituted by one or more ketone functions, they are preferred to be a ketone function at 3, at 7, at 11 or at 12.

When the A,B,C and D rings are substituted by one or more halogen atoms, it is preferred that there be a fluorine, chlorine or bromine atom at position 6 or 9 αfor example. When the A,B,C and D rings are substituted by one or more alkyls, it is preferred that there be a methyl or methyl at positions 2,6,7, at 16α or at 16β. When the A,B,C and D rings are substituted by one or more alkoxy it is preferred that there be a methoxy or ethoxy at position 3 or 11β. When the A,B,C and D rings are substituted by one or more alkenyl, it is preferred that there be a vinyl or an allyl at position 11β, for example. When the A,B,C and D rings are substituted by one or more alkynyl, it is preferred that there be an ethynyl at position 11β, for example.

The hydroxyl groups can be protected by the usual methods known in the literature. For example, there can be cited, the acetonide, cyclic carbonates, orthoesters, cyclic sulfites, ether formed with tetrahydropyrannyl, trityl or benzyl, acyls such as acetyl, succinyl or formyl. The ketone groups can also be protected by the standard protective groups such as ketals, especially ethylene ketal, thioketals, hemithoketals, enol ethers, enol acetates, enamines and oximes. However, the ketal groups and especially ethylene ketal is preferred to protect the ketone groups. When the products of formula I include a ketone in 3-position, this group is very preferentially protected.

The radicals $R_3$ and $R_4$, being identical or different, can be hydrogen or methyl, ethyl or propyl, for example. Products in which $R_3$ and $R_4$ each are methyl are, however, preferred. The double bond at position 22(23) can be in the E or Z form, or in the form of a mixture of E and Z isomers Among the preferred compounds of the invention are the products of formula I wherein $R_1$ and $R_2$ each are methyl and wherein the A,B,C and D rings have at position 3 a possibly protected hydroxyl, and possibly one or more other functions chosen from possibly protected hydroxyl at position 6,7,11 and 12, and possibly protected ketones at positions 7, 11 and 12.

Among the preferred products of formula I are those wherein the A,B,C and D rings carry at position 3 a possibly protected hydroxyl function, and, possibly, one or more other functions chosen from the possibly protecting hydroxyl at positions 6,7 or 12, and the possibly protected ketones at positions 7,11 or 12.

In this latter family, there can be cited the products which comprise, as the skeleton of the rings, A,B,C and D, those of the products derived from the natural or semi-synthetic bile acids. These products can be tabulated as follows

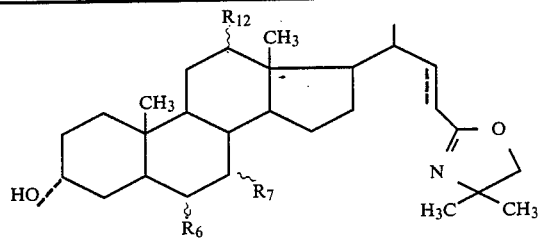

| $R_6$ | $R_7$ | $R_{12}$ |
|---|---|---|
| H | OHα | OHα |
| H | OHβ | OHα |
| H | H | H |
| H | H | OHα |
| H | OHα | H |
| OHα | H | H |
| H | OHβ | H |
| OHα | OHα | H |
| OHβ | OHα | H |
| OHβ | OHβ | H |
| H | H | OHα |

In these products the hydroxy(s) can also be protected, notably the hydroxyl in position 3. The preferred protector group is acetyl.

Among the products having one or more ketone functions, the following products are preferred

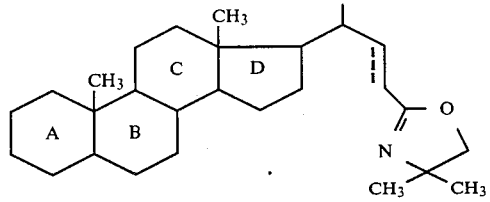

| 3 protected ketone | | | | | |
|---|---|---|---|---|---|
| 3 OHα, | 7 keto, | 12 OHα | | | |
| 3 OHα | 11 keto | | | | |
| 3 OHα | 7 OHα, | 12 keto | 3 OH, | 11 Keto, | 12 OH |
| 3 OHα, | 7 keto | | | | |
| 3 OHα, | 7 OHβ | 12 keto | | | |

As before, the hydroxyl functions can be protected and the same is true for the 7- or 12- ketone functions. The preferred protector group for the ketone function is a cyclic or non-cyclic ketal.

The preferred products are 23-(4,5-dihydro-4,4-dimethyl-2-oxazolyl)-(3α,5β)-24-nor-cholan-3-ol-11-one and the corresponding 3-acetyloxy compound and 23-(4,5-dihydro-4,4-dimethyl-2-oxazolyl)-(3α, 5β) 24-nor-Δ²²-cholan-en-3-ol-11-one and its corresponding 3-acetoxy compound.

The process of the invention for the preparation of compounds of formula I comprises reacting a compound of the formula

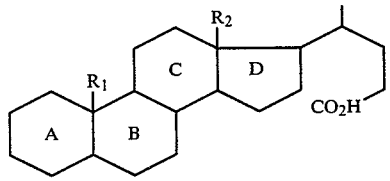

II wherein A,B,C,D, R₁ and R₂ have the above definition with a compound of the formula

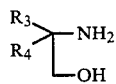

III wherein R₃ and R₄ have the above definition to obtain a compound of the formula

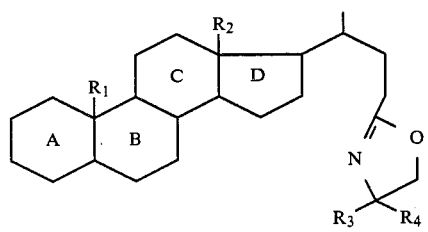

Ia which is treated, if desired, with an oxidizing reagent to obtain a compound of the formula

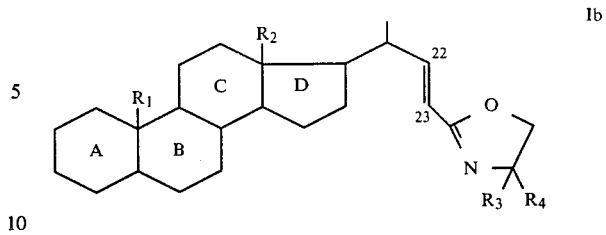

Ib wherein the 22(23) double bond is in the E or Z form or in the form of a mixture of E and Z isomers.

It is preferred to use a compound of formula III wherein $R_3$ and $R_4$ each are methyl which is 2-amino-2-methylpropanol and the reaction is preferably carried out at reflux of an organic solvent such as xylene. It is preferred to operate in the presence of a mild acid such as boric acid or of a resin such as DOWEX 50W resin.

The oxidizing reagent can be seleninic anhydride used in stoichiometric amounts in the conditions described, for example, in JCS Chem. Comm. 1978, p 952-4. The operation is effected in an organic solvent such as pyridine or methylethylpyridine or a mixture of solvents such as pyridine-tetrahydrofuran. It is also possible to operate in the presence of a catalytic amount of phenylseleninic anhydride, regenerated in situ by oxidation of the diphenyldiselenide resulting from the reduction of phenylseleninic anhydride. The operation is effected under the conditions described in JCS Chem. Comm. 1981, p. 1,044-5 in the presence of metaiodoxy benzoic acid or of an encumbered derivative of this acid such as

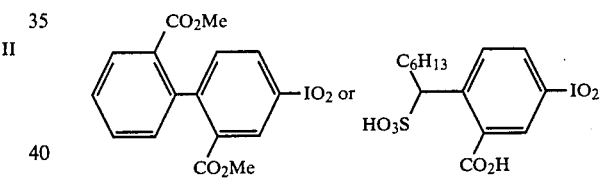

Preferably, the reaction is effected at reflux of an organic solvent such as toluene or in a solvent such as benzene or chlorobenzene. There can also be used as oxidizing agent phenylseleninic acid in a solvent or a mixture of solvents such as acetone and pyridine or methyl ethylpyridine. The preferred oxidizing reagent to convert the compunds of formula Ia to those of formula Ib is chosen from the group of phenyl seleninic anhydride, possibly prepared in situ and phenyl seleninic acid.

The process of the invention can be used with very varied products of formula II. Particularly, the starting product of formula II can include blocked or non-blocked reactive functions. When the starting product of formula II includes reactive functions, especially a 3-hydroxyl, this function can either be blocked, or free throughout the synthesis. It is also possible to start with a product of formula II in which the reactive function or functions are free, and block them during the synthesis.

It is preferred to protect the hydroxyl group, notably the 3-position in the products of formula Ia before oxidizing them into products with the formula Ib. When seleninic anhydride is used as the oxidizing reagent, it is preferred to operate on the products of formula Ia in which the 3-hydroxy is blocked. As indicated previously a protective acyl group and particularly acetyl, is preferred. The protection step, preferably acetylation, is carried out in the usual manner and it is preferred to operate in the presence of an anhydride preferably acetic anhydride, and with 4-dimethylamino-pyridine as catalyst. The operation can be in an organic solvent such as methylene chloride.

The novel process for the preparation of 20-keto-pregnanes comprises reacting a compound of the formula

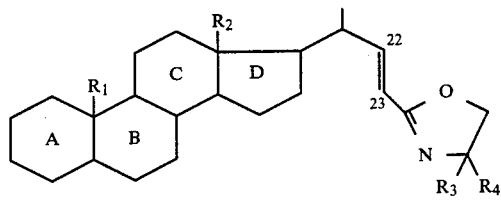

with a reagent capable causing migration of double bonds to obtain a compound of the formula

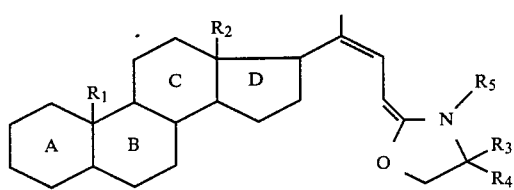

wherein $R_5$ is hydrogen or an organic residue and reacting the latter with an oxidizing agent to obtain a compound of the formula

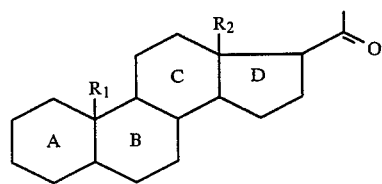

wherein A,B,C,D, $R_1$ and $R_2$ have the above definitions.

The double-bond migration reagent is very preferably phosgene and the reaction is effected in a solvent such as toluene in the presence of a base such as triethylamine to obtain a product in which $R_5$ is —COCl. A reagent of the formula $CCl_3 COCl$ can also be used. The oxidizing reagent is preferably ozone and the reaction is effected in an organic solvent such as methylene chloride. Chromic anhydride may, however, be used.

In a preferred embodiment of the latter process, a compound of formula Ib is reacted with phosgene to obtain a compound of formula IV wherein $R_5$ is —COCl and the latter in methylene chloride is reacted with ozone.

In a variation of the process to prepare a compound of formula V, a compound of the formula

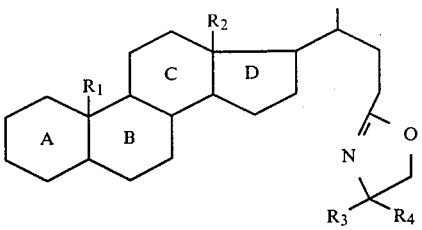

is reacted with an oxidizing reagent, preferably at reflux of an organic solvent such as benzene or toluene and the reaction lasts many hours. Preferably, the oxidizing reagents described above are used, and especially phenylseleninic acid or diphenyldiselenide in the presence of iodoxybenzene. During this oxidization, the functional groups at the A,B,C and D rings may also be oxidized, particularly hydroxyl groups which the molecule may include. Also during this reaction, one or more double bonds may be formed.

A preferred mode of the invention comprises oxidizing 23-(4,5-dihydro-4,4-dimethyl-2-oxazolyl)-(3α, 5β)-24-nor-cholane-3-ol-11-one to form $\Delta^{1,4}$-pregnadiene 3,11,20-trione.

The novel intermediates of the invention are the compounds of the formula

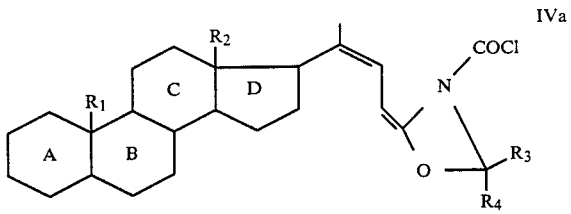

wherein A,B,C,D,$R_1$,$R_2$,$R_3$ and $R_4$ have the above definitions.

The products of formula II used as starting materials are known compounds and many are natural products of the bile acid series, or products which can be prepared by the usual methods starting from these natural products.

The compounds of formula V are known products of the progesterone series having useful pharmacological properties. Moreover, these compounds are useful for the reconstruction of the desoxycortisone chain,

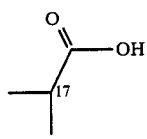

or for other chains in the 17-position.

In the following examples there are described several preferred embodiments to illustrate the invention. However, it should be understood that the invention is not intended to be limited to the specific embodiments.

EXAMPLE 1

3-acetyloxy (3α,5β) pregnane-11,20-dione

STEP A:
23-(4,5-dihydro-4,4-dimethyl-2-oxazolyl)(3α,5β)-24-nor-cholan-3-ol-11-one A mixture of 3.2 g of (3α,5β) cholan-3-ol-11-one-24-oic acid, 1 g of 2-amino-2-methyl-propanol and 200 mg of boric acid was refluxed in 60 ml of xylene with azeotropic elimination of water for 40 hours and the solvent was eliminated under vacuum. The residue was taken up in 50 ml of hot methanol and 100 ml of water were added. The mixture was refluxed for one hour, then cooled, and the white solid was filtered off and dried to obtain 3.5 g (96%) of 23-(4,5-dihydro-4,4-dimethyl-2-oxazolyl)(3α,5β)-24-nor-cholan-3-ol-11-one melting at 163°–165° C. (EtOAc) and having a specific rotation of $[\alpha]_D = +47°$ (c=0.5% in CHCl$_3$)

IR Spectrum (nujol): 3,330; 1,703; 1,660 cm$^{-1}$.

NMR Spectrum (ppm): (CDCl$_3$) 3,80 (s,2H); 3.50 (s, 1H, 3β-H); 1.20 (s, 6H); 1.10 (s, 3H, 10-Me); 0.60 (s, 3H, 13-Me)

| Analysis: C$_{28}$H$_{45}$NO$_3$ | | | |
|---|---|---|---|
| | % C | % H | % N |
| Calculated: | 75 | 10.22 | 3.16 |
| Found: | 75.55 | 10.11 | 3.16 |

STEP B:
3-acetyloxy-23-(4,5-dihydro-4,4-dimethyl-2-oxazolyl)-(3α,5β)-24-nor-cholan-11-one 2.5 g of the product of Step A were dissolved in a mixture of 10 ml of dichloromethane and 5 ml of acetic anhydride containing 200 mg of 4-dimethylamino-pyridine and the mixture was left at ambient temperature for 1 hour, then was washed with an aqueous solution of 5% potassium carbonate, dried and filtered over silica. The evaporation of the solvent yielded 2.72 g of 3-acetyloxy-23-(4,5-dihydro-4,4-dimethyl-2-oxazolyl)-(3α,5β)-24-nor-cholan-11-one (yield=100%) which was used as is for the following step.

STEP C:
3-acetyloxy-23-(4,5-dihydro-4,4-dimethyl-2-oxazolyl)-(3α,5β)-24-nor-Δ$^{22}$-cholen-11-one 155 mg of the product of Step B were dissolved in 5 ml of pyridine and 225 mg of phenylselininic anhydride were added. The mixture was heated to 60° C. for 6 hours and was then poured into a 5% aqueous solution of potassium carbonate and extracted with dichloromethane. The organic phase was washed with water, then dried over K$_2$CO$_3$, and evaporated to dryness. The residue was chromatographed on silica and eluted with a 1:1 mixture of dichloromethane and hexane to eliminate the diphenyl diselenide (Ph Se Se Ph) and then with ether to obtain 155 g of white crystals of 3-acetyloxy-23-(4,5-dihydro-4,4-dimethyl-2-oxazolyl)-(3α,5β)-24-nor-Δ$^{22}$-cholen-11-one (Yield=100%) melting at 158°–163° C. (ether) and having a specific rotation of $[\alpha]_D = 49°$ (c=0.5% in CHCl$_3$).

IR Spectrum (CH$_2$Cl$_2$): 1,720, 1,700, 1,670 and 1,605 cm$^{-1}$

NMR Spectrum (ppm): 6.35 and 6.20 (dd, J=15 and 7H$_z$, 1H, 22-H); 5.70 (d, J=15H$_z$, 1H, 23-H); 4.60 (wide, 1H, 3β-H); 3.82 (s, 2H); 1.25 (s, 6H); 1.17 (s, 3H, 10-Me); 0.65 (s, 3H, 13-Me).

| Analysis: C$_{30}$H$_{45}$NO$_4$ | | | |
|---|---|---|---|
| | % C | % H | % N |
| Calculated: | 74.50 | 9.38 | 2.90 |
| Found: | 74.27 | 9.51 | 3.13 |

STEP D:
2-[3-acetyloxy-(3α,5β)-24-nor-Δ$^{20(22)}$-cholen-11-one-23-ylidene]-4,4-dimethyl-3-oxazolidinecarbonyl chloride A solution of 75 mg of phosgene in 0.4 ml of toluene was added to a solution of 86 mg of the product of Step C in a mixture of 4 ml of toluene and 0.5 ml of triethylamine, and the mixture was stirred at ambient temperature for 30 minutes. The reaction mixture was filtered and the solid of triethylamine hydrochloride was washed with a little dry toluene. The toluene was then evaporated to dryness and 2-[3-acetyloxy-(3α,5β)-24-nor-Δ$^{20(22)}$-cholen-11-one-23-ylidene]-4,4-dimethyl-3-oxazolidinecarbonyl chloride was isolated and used as is for the following step.

STEP E: 3-acetyloxy-(3α,5β)pregnane-11,20-dione

The product of Step D was taken up in 5 ml of methylene chloride and a current of ozone was passed into this solution cooled to 0° C. until complete disappearance of the starting compound. An excess of dimethyl sulfide was added to reduce the ozonides formed and the solution was filtered over alumina to obtain 61 mg of 3-acetyloxy-(3α,5β) pregnane-11,20-dione in the form of a colorless oil which crystallized slowly. (Yield 90%). The product melted at 130°–133° C. and had a specific rotation of $[\alpha]_D = +125°$ (c=1.3% in CHCl$_3$).

EXAMPLE 2

23-[4,5-dihydro-4 4-dimethyl-2-oxazolyl] (3α,5β)-24-nor-Δ$^{22}$-cholen-3-ol-11-one STEP A: 23-[4,5-dihydro-4,4-dimethyl-2-oxazolyl) (3α,5β)-24-nor-cholan-3-ol-11-one Using the process of Step A of Example 1, 12.9 g of (3α,5β) cholan-3-ol-11-one-24-oic acid were reacted to obtain 14 g of 23-[4,5-dihydro-4,4-dimethyl-2-oxazolyl) (3α,5β)-24-nor-cholan-3-ol-11-one, identical to that of Example 1, Step A.

STEP B: 23-[4,5-dihydro-4,4-dimethyl-2-oxazolyl] (3α,5β)-24-nor-Δ$^{22}$-cholen-3-ol-11-one 106 mg of the product of Step A were dissolved in a mixture of 5 ml of tetrahydrofuran and 1 ml of pyridine and the mixture was heated to 60° C. 190 mg of phenylseleninic anhydride were added to the mixture which was then left at 60° C. for 1 hour, after which it was cooled to 20° C. 2 ml of 33% hydrogen peroxide were then poured in with strong stirring which was maintained for 20 minutes. The mixture was then poured into an aqueous solution of 5% potassium carbonate and extracted with dichloromethane. The organic phase was washed with water, then dried and evaporated to dryness. The residue was chromatographed over silica and eluted with ethyl acetate to obtain 106 mg of 23-[4,5-dihydro-4,4-dimethyl-2-oxazolyl] (3α,5β)-24-nor-Δ$^{22}$-cholen-3-ol-11-one (yield=100%) melting at 203°–205° C. (ether) and having a specific rotation of [α]$_D$=+37° (c=0.6% in CHCl$_3$).

IR Spectrum (Nujol): 1,690, 1,665 and 1,601 cm$^{-1}$.

NMR Spectrum (ppm): 6.60 and 6.30 (dd, J=9 H$_z$ and 16 H$_z$, 1H, 22-H); 5.85 (d,J=16H, 1H, 23-H); 3.65 (1H, 3β-H); 1.31 (s, 6H); 1.18 (s, 3H, 10-Me); 0.67 (s, 3H, 13-Me).

| Analysis: C$_{28}$H$_{43}$NO$_3$ | | | |
|---|---|---|---|
| | % C | % H | % N |
| Calculated: | 76.15 | 9.81 | 3.17 |
| Found: | 76.02 | 10.05 | 3.28 |

STEP B: 23-(4,5-dihydro-4,4-dimethyl-2-oxazolyl) (3α,5β)-24-nor-Δ$^{22}$-cholen-3-ol-11-one 3.2 g of the product of Step A of Example 1 were dissolved in a mixture of 60 ml of acetone and 0.6 ml of pyridine and the mixture was heated to 50° C. 5 g of phenylseleninic acid were added thereto and after heating for 1 hour, the mixture was poured into a 5% solution of potassium carbonate. The precipitate obtained was taken up, after drying, in dichloromethane and 20 ml of 33% hydrogen peroxide were added at a temperature below 10° C., with strong stirring. The organic phase was washed with an aqueous solution of 5% potassium carbonate and evaporated to dryness to obtain 2.5 g of 23-(4,5-dihydro-4,4-dimethyl-2-oxazolyl) (3α,5β)-24-nor-Δ$^{22}$-cholen-3-ol-11-one, identical to that obtained at Step B (yield≈80%).

The aqueous phases were combined and neutralized with concentrated hydrochloric acid to a pH of 7, and at 20° C., 15 g of sodium hydrosulfite were added. After stirring for 1 hour at 20° C., and filtering and drying, 3.8 of diphenyldiselenide were obtained. (yield≈92%).

EXAMPLE 3

3-acetyloxy-(3α,5β)-pregnane-11,20-dione

STEP A: 23-(4,5-dihydro-4,4-dimethyl-2-oxazolyl) (3α,5β)-24-nor-cholan-3-ol-11-one A mixture of 29.3 g of (3α,5β)-cholan-3-ol-11-one-24-oic acid, 8 g of 2-amine-2-methy-1-propanol and 1 g of boric acid was refluxed in 150 ml of xylene for 40 hours, while eliminating the water azeotropically. The solvent was evaporated under reduced pressure and the residue was taken up in 125 ml of hot methanol. 250 ml of water were added, and the mixture was refluxed for 1 hour After cooling, the precipitate was separated to obtain 32 g of 23-(4,5-dihydro-4,4-dimethyl-2-oxazolyl) (3α,5β)-24-nor-cholen-3-ol-11-one in the form of a white solid melting at 163°–165° C.

STEP B: 3-acetyloxy-23-(4,5-dihydro-4,4-dimethyl-2-oxazolyl) (3α,5β)-24-nor-cholan-11-one 25 g of the product of Step A were dissolved in a solution of 80 ml of methylene chloride, 12 ml of acetic anhydride and 1 g of 4-dimethylamino-pyridine. The solution was stirred for 1 hour at ambient temperature and then was washed three times with 50 ml of a 5% aqueous solution of potassium carbonate. The organic phase was dried over potassium carbonate and was filtered over silica. The solvent was evaporated under reduced pressure to obtain 27.2 g of 3-acetyloxy-23-(4,5-dihydro-4,4-dimethyl-2-oxazolyl) (3α,5β)-24-nor-cholan-11-one which was used as is in the next step.

STEP C: 3-acetyloxy-23-(4,5-dihydro-4,4-dimethyl-2-oxazolyl) (3α,5β)-24-nor-Δ$^{22}$-cholen-11-one 27.2 g of acetate of Step B were dissolved in 200 ml of anhydrous methyl ethyl pyridine, and 29.5 g of phenylseleninic anhydride were added thereto. The mixture was heated to 60° C. and stirred for 6 hours and then was poured into 150 ml of a 5% aqueous solution of potassium carbonate. After extraction with methylene chloride, the organic phase was washed with water, dried over potassium carbonate, and evaporated to dryness under reduced pressure. The residue was chromatographed over silica and eluted with a 1:1 mixture of methylene chloride and hexane and then with ether to obtain 27.2 g of 3-acetyloxy-23-(4,5-dihydro-4,4-dimethyl-2-oxyzolyl) (3α,5β)-24-nor-Δ$^{22}$-cholen-11-one in the form of white crystals melting at 158°–163° C. (yield=100%).

STEP C': 3-acetyloxy-23-(4,5-dihydro-4,4-dimethyl-2-oxazolyl) (3α,5β)-24-nor-Δ$^{22}$-cholen-11-one A mixture of 27.2 g of acetate of Step B, 180 ml of anhydrous acetone and 20 ml of anhydrous methyl ethyl pyridine was heated to 50° C. and 15.6 g of phenyl seleninic acid were added thereto. After heating for 1 hour at 50° C., the mixture was poured into 150 ml of a 5% aqueous solution of potassium carbonate. The precipitate, previously dried, was taken up in 150 ml of methylene chloride, and the solution was cooled below 10° C. Under strong stirring, 80 ml of 33% hydrogen peroxide was added dropwise and the organic phase was washed twice with an aqueous solution of potassium carbonate, then dried and evaporated to dryness under reduced pressure to obtain 27.2 g of 3-acetyloxy-23-(4,5-dihydro-4,4-dimethyl-2-oxazolyl) (3α,5β)-24-nor-Δ$^{22}$-cholen-11-one in the form of white crystals melting at 158°–163° C.

STEP C'': 3-acetyloxy-23-(4,5-dihydro-4,4-dimethyl-2-oxazolyl) (3α,5β)-24-nor-22-cholen-11-one 17.1 g of m-iodoxy benzoic acid and 1.75 g of diphenyl diselenide were dissolved in 150 ml of anhydrous toluene and the solution was refluxed for 15 minutes until the yellow color disappeared. 27.2 g of the acetate ot Step B were then added and reflux was continued for two and a half hours. Then, the mixture was cooled and washed with 75 ml of a saturated solution of sodium bicarbonate. The organic phase was washed with water, dried and evaporated to dryness under reduced pressure to obtain 27.2 g of 3-acetyloxy-23-(4,5-dihydro-4,4-dimethyl--2-oxazolyl) (3α,5β)-24-nor-Δ$^{22}$-cholen-11-one in the form of white solid melting at 158°–163° C.

STEP D: 2-[3-acetyloxy-(3α,5β)-24-nor-Δ$^{20(22)}$-cholen-11-one-23-yl-idene]-4,4-dimethyl-3-oxazolidine carbonyl chloride 21.5 g of the product of Step C were dissolved in 150 ml of anhydrous toluene and 12.5 ml of anhydrous triethylamine and a solution of 7 g of phosgene in 30 ml of anhydrous toluene was added little by little. The mixture was stirred at ambient temperature for half an hour and then the precipitate was filtered and washed with 30 ml of anhydrous toluene. The filtrate was evaporated under reduced pressure and the product was used for the following step as is.

STEP E: 3-acetoxy-(3α,5β)-pregnane-11,20-dione

The product of Step D was dissolved in 150 ml of methylene chloride and the solution was cooled to 0° C. A current of ozone was passed therethrough until the starting product disappeared. An excess of dimethyl sulfide was added and the solution was filtered over alumina to obtain 15 g of 3-acetoxy-(3α,5β)-pregnane-11,20-dione in the form of a colorless oil which crystallized slowly. It melted at 130°–133° C.

EXAMPLE 4
(3α,5β)pregnane-3-ol-11,20-dione

A solution of 365 mg of 23-[4,5-dihydro-4,4-dimethyl-2-oxazolyl) (3α,5β)-24-nor-cholan-3-ol-11-one of Step A of Example 1 and 457 mg of phenylseleninic acid in 10 ml of dichloromethane and 1 ml of pyridine was refluxed for 6 hours and excess phenylseleninic acid was reduced by 455 mg of sodium dithionite dissolved in a minimum of water. The mixture was filtered over potassium carbonate and sodium dithionite and 0.5 ml of trichloroacetyl chloride was then added dropwise to the solution cooled to 0° C. The mixture was held for 4 hours at this temperature, after which it was diluted with 10 ml of dichloromethane and treated with 1.7 g of potassium carbonate in a minimum of water. After stirring for a few minutes, the mixture was ozonolyzed for 20 minutes at 0° C. 2 ml of dimethyl sulfide were added, and the mixture was evaporated to dryness under reduced pressure. The residue was taken up in 20 ml of methanol and the solution was treated with 0.5 ml of 30% aqueous sodium hydroxide, kept at ambient temperature for 20 minutes and was extracted with dichloromethane. The organic phase was washed with water. The washing waters were neutralized with hydrochloric acid and treated with an excess of sodium dithionite to obtain, after extraction, 377 mg of diphenyldiselenide. The organic phase was dried and evaporated to dryness under reduced pressure, the residue was chromatographed over silica and eluted with ethyl acetate-hexane (9:1) to obtain 219 mg of (3α,5β)pregnane-3-ol-11,20-dione melting at 174°–176° C. and having a specific rotation of $[\alpha]_D = 109°$ (c=1% in CHCl$_3$).

IR Spectrum, max (nujol): 3,250, 1,690 cm$^{-1}$
NMR Spectrum (ppm): 2.16 (3H, s), 1.18 and 0.58 (6H, 2 s).

EXAMPLE 5
3-acetoxy-(3α,5β)-pregnane-11,20-dione

A mixture of 232 mg of 3-acetoxy-23-[4,5-dihydro-4,4-dimethyl-2-oxazolyl] (3α,5β)-24-nor-cholan-11-one of Step B of Example 1, 28 mg of phenylseleninic acid, 594 mg of iodoxybenzene an 10 ml of benzene was refluxed for 8 hours and the solvent was evaporated under reduced pressure. The residue was chromatographed over silica and eluted with ethyl acetate-hexane (1:1) to obtain 72 mg of 3-acetoxy-(3α,5β)pregnane-11,20-dione.

EXAMPLE 6
Δ$^{1,4}$-pregnadiene-3,11,20-trione

A mixture of 62 mg of diphenyldiselenide and 1.4 g of iodoxybenzene in 30 ml of toluene was refluxed until the yellow color disappeared and 440 mg of 23-(4,5-dihydro-4,4-dimethyl-2-oxazolyl) (3α,5β)-24-nor-cholan-3-ol-11-one of Step A of Example 1 were added. Heating was maintained for 6 to 7 hours and after filtering, evaporating the solvents and chromatographing the residue over silica (eluent:dichloromethane-ether), 40 mg of Δ1,4-pregnadiene-3,11,20-trione in the form of yellow oil were obtained which crystallized slowly and melted at 163°–168° C.

Various modifications of the products and process of the invention may be made without departing from the spirit or scope thereof and it is to be understood that the invention is intended to be limited only as defined in the appended claims.

What is claimed is:

1. A steroid of the formula

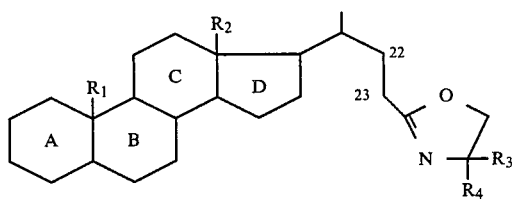

wherein R$_1$ is selected from the group consisting of hydrogen and methyl, R$_2$ is selected from the group consisting of methyl and ethyl, R$_3$ and R$_4$ are individually selected from the group consisting of hydrogen and alkyl of 1 to 4 carbon atoms, the A,B,C and D rings may contain 1 to 3 double bonds and may be optionally substituted with one or more members of the group consisting of —OH, protected hydroxyl, =O, protected keto, halogen, alkyl or alkoxy of 1 to 4 carbon atoms and alkenyl and alkynyl of 2 to 4 carbon atoms.

2. A compound of claim 1 wherein R$_1$ and R$_2$ are methyl.

3. A compound of claim 2 optionally containing a 3-OH or protected 3-OH, optionally one or more hydroxy in the 6,7,11 or 12-position optionally protected or, one or more optionally protected keto in the 7,11 or 12-position.

4. A compound of claim 1 selected from the group consisting of 23-(4,5-dihydro-4,4-dimethyl-2-oxazolyl) (3α,5β)-24-nor-cholan-3-ol-11-one and its 3-acetyloxy derivative.

5. A process for the preparation of a compound of the formula

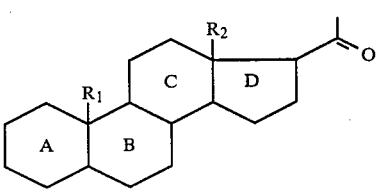

wherein A,B,C,D,R$_1$ and R$_2$ have the significance of claim 1 comprising reacting a compound of the formula with a double-bond migration reagent to obtain a compound of the formula

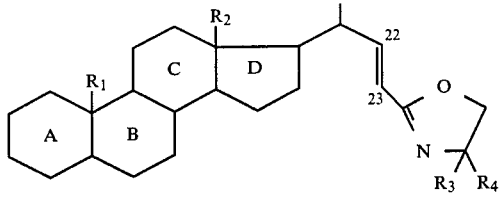

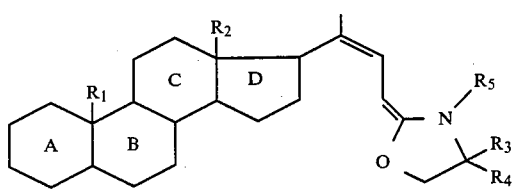

wherein $R_5$ is hydrogen or a residue of an organic group and reacting the latter with an oxidizing reagent to obtain a compound of formula V.

6. The process of claim 5 wherein the double-bond migration reagent is phosgene whereby $R_5$ is —COCl.

7. A process for the preparation of a compound of the formula

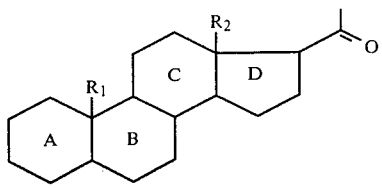

wherein A,B,C,D,$R_1$ and $R_2$ have the significance of claim 1 comprising reacting a compound of the formula

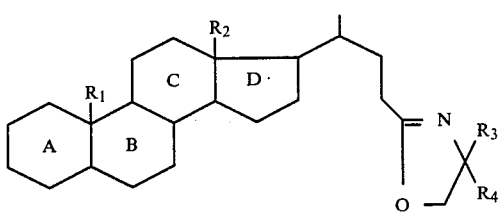

with an oxidizing agent.

8. The process of claim 7 wherein the starting compound is 23-(4,5-dihydro-4,4-dimethyl-2-oxazolyl)(3α,5β)-24-nor-cholane-3-ol-11-one to form $\Delta^{1,4}$-pregnadine-3,11,20-trione.

9. A compound of the formula

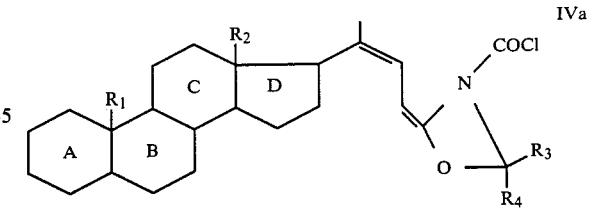

wherein A,B,C,D,$R_1$,$R_2$,$R_3$ and $R_4$ have the significance of claim 1.

* * * * *

UNITED STATES PATENT AND TRADEMARK OFFICE
CERTIFICATE OF CORRECTION

PATENT NO. : 4,689,410
DATED : Aug. 25, 1987
INVENTOR(S) : DEREK H.R. BARTON; SAMIR Z. ZARD; JOCELYNE WOZNIAK

It is certified that error appears in the above-identified patent and that said Letters Patent is hereby corrected as shown below:

Col.  Line
 12    20

"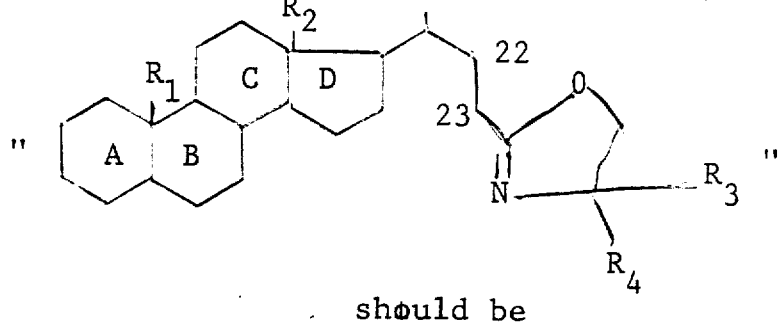"

should be

-- 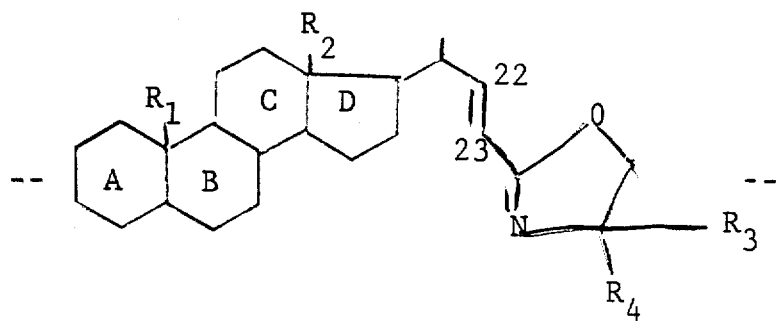 --

Signed and Sealed this

Twelfth Day of April, 1988

Attest:

DONALD J. QUIGG

Attesting Officer    Commissioner of Patents and Trademarks